United States Patent [19]
Jarman

[11] Patent Number: 5,842,979
[45] Date of Patent: Dec. 1, 1998

[54] METHOD AND APPARATUS FOR IMPROVED PHOTOPLETHYSMOGRAPHIC MONITORING OF OXYHEMOGLOBIN, DEOXYHEMOGLOBIN, CARBOXYHEMOGLOBIN AND METHEMOGLOBIN

[75] Inventor: Kristin Hoyer Jarman, Lafayett, Colo.

[73] Assignee: Ohmeda Inc., Liberty Corner, N.J.

[21] Appl. No.: 800,372

[22] Filed: Feb. 14, 1997

[51] Int. Cl.⁶ ......................................................... A61B 5/00
[52] U.S. Cl. ............................................................... 600/322
[58] Field of Search .................................... 600/310, 311, 600/322, 323, 324, 330; 356/39, 41

[56] References Cited

U.S. PATENT DOCUMENTS

| | | | |
|---|---|---|---|
| 4,167,331 | 9/1979 | Nielsen | 600/322 |
| 5,553,615 | 9/1996 | Carim et al. | 600/324 |
| 5,638,816 | 6/1997 | Kiani-Azarbayjany et al. | 356/39 |

FOREIGN PATENT DOCUMENTS

WO 97/47233  12/1997  WIPO .

Primary Examiner—Jennifer Bahr
Assistant Examiner—Eric F. Winakur
Attorney, Agent, or Firm—Roger M. Rathbun

[57] ABSTRACT

An improved method and apparatus for the photoplethysmographic monitoring of blood analyte parameters, specifically oxyhemoglobin, deoxyhemoglobin (reduced hemoglobin), carboxyhemoglobin and methemoglobin, uses a plurality of beams of light having different spectral contents to trans-illuminate the tissue of a patient. Received light is measured and the normalized differential absorption is used in a forward calibration equation to generate estimated relative blood analyte concentration values. Error in the blood analyte concentration values is minimized by applying constraints to the estimated analytes. Specifically, the constraints require that all relative analyte concentration values are greater than or equal to zero and sum to one hundred percent. An alternate method of applying constraints to the determination of the stabilized analyte concentration values reduces computation time by using an inverse calibration equation and substituting the inverse equation for the forward equation in the minimization process.

13 Claims, 5 Drawing Sheets

METHOD AND APPARATUS FOR IMPROVED PHOTOPLETHYSMOGRAPHIC MONITORING OF OXYHEMOGLOBIN, DEOXYHEMOGLOBIN, CARBOXYHEMOGLOBIN AND METHEMOGLOBIN

BACKGROUND OF THE INVENTION

The present invention generally concerns the monitoring of a patient's tissue using a photoplethysmographic device to generate information related to the concentration of oxyhemoglobin (O2Hb), deoxyhemoglobin or reduced hemoglobin (RHb), carboxyhemoglobin (COHb) and methemoglobin (MetHb) in a patient's blood. More particularly the present invention concerns improvements to the accuracy of these measurements which can be obtained through the application of a specific stabilization method and apparatus.

During emergency evaluation, surgery and other medical procedures, clinicians often want to know the oxygen concentration of the blood, as well as other factors. In pulse oximetry the relative concentration of oxyhemoglobin and deoxyhemoglobin is measured as a percentage of total hemoglobin in order to provide data on the oxygenation of the patient's blood. Blood oxygenation can be adversely affected by the generation of additional hemoglobin species, called dyshemoglobins. Most notably, carboxyhemoglobin is generated when carbon monoxide molecules bind to hemoglobin in the blood. An accurate measurement of carboxyhemoglobin concentration in the patient's blood may be needed when the patient is a smoker or if carbon monoxide poisoning is suspected. Additionally, elevated methemoglobin levels in the blood can be caused by various medications, illegal drugs and certain pathological conditions such as sickle cell anemia. Therefore measurement of the methemoglobin concentration is also useful during patient evaluation. Pulse-oximeters have been commercially available for measuring the oxygen saturation, or concentration of oxyhemoglobin as a percent of total hemoglobin, in arterial blood. These instruments rely on time-varying absorption of light by tissue supplied with pulsating arterial blood with a technique known generally as photoplethysmography. Conventional pulse oximeter instruments transmit light at two different center wavelengths through tissue. The spectral characteristics of oxygenated hemoglobin and reduced hemoglobin in arterial blood differ for the two different light signals emitted by the pulse oximeter instrument. Since the arterial blood pulsates, the light transmitted through the tissue generally exhibits a time-varying component, as well as a time-invariant component. From a ratio formed by dividing a ratio of the time-varying component to the time-invariant component of the light intensity from one emitter transmitted through the tissue by the ratio of the time-varying component to the time-invariant component of the transmitted intensity from the second emitter, the degree of oxygen saturation in the arterial blood can be determined. See, for example, an article by J. A. Pologe in *International Anesthesiology Clinics,* Volume 25, pp. 137–153 (1987).

The basic physical property that allows the measurement of arterial oxygen saturation by pulse oximetry is that the blood changes color with saturation. A pulse oximeter measures the "color" of the arterial blood and correlates this "color" to a given oxygen saturation to be displayed. When blood is well oxygenated it does not absorb a great deal of red light but as it desaturates it absorbs more and more red light giving the blood a darker appearance. The opposite behavior occurs in the near infrared region (from about 810 nanometers to 1000 nanometers) where hemoglobin absorbs more light when saturated with oxygen than when desaturated. For this reason current pulse oximeters use two emitters, usually light emitting diodes, one designed to generate light in the red region, usually centered around 660 nanometers, and one which generates light in the near infrared region usually centered around 925 or 940 nanometers.

The most obvious limitation of pulse oximetry derives from the fact that it is only a two channel system (channel defined as the light or electronic representation of light out of the tissue originating from any given emitter). Therefore any conventional pulse oximeter can only solve for two blood analytes and makes the assumption that only oxyhemoglobin and reduced hemoglobin are present in the arterial blood. Any additional chromophores that are present in arterial blood and which absorb light in the wavelength bands used by the instrument will lead to erroneous readings. Two such chromophores include carboxyhemoglobin and methemoglobin. In particular, if carboxyhemoglobin or methemoglobin is present in above normal levels, a conventional pulse oximeter will give falsely high readings for the arterial oxygen saturation. This is one of the most serious and potentially dangerous limitations of current pulse oximetry.

Prior art pulse oximeters have so far lacked a means to compensate for errors in the measurement of oxyhemoglobin and reduced hemoglobin due to the presence of carboxyhemoglobin and methemoglobin in the blood. The manufacture of non-invasive devices which measure oxyhemoglobin, deoxyhemoglobin, carboxyhemoglobin and methemoglobin concentrations has been attempted by others. However, there has been no successful low-cost commercial implementation of a photoplethysmographic monitor which is capable of accurately measuring these four blood analytes.

The present invention overcomes this deficiency by providing novel methods and apparatus for stabilizing the estimated concentrations of oxyhemoglobin, reduced hemoglobin, carboxyhemoglobin and methemoglobin which are generated by a photoplethysmographic instrument. This stabilization method uses additional information in estimating the analyte concentrations, namely that the analyte concentrations must lie between 0 and 100% and must total 100%. While many current pulse oximeters constrain the displayed oxygen saturation reading to fall within 0 to 100%, none use this information in the actual analyte estimation process. The present invention significantly improves the accuracy of the blood analyte readings by incorporating these constraints into the analyte estimation calculations.

BRIEF SUMMARY OF THE INVENTION

This application discloses a photoplethysmographic method and apparatus for the accurate continuous, real-time, noninvasive measurement of a plurality of blood analyte concentrations, particularly the concentrations (as a percent of total hemoglobin) of the oxyhemoglobin, deoxyhemoglobin, carboxyhemoglobin and methemoglobin levels in blood.

The method of the invention relies on the principle that these four analyte levels are interrelated. Each of the four analyte levels must be between 0% and 100%, and barring the presence of any other hemoglobin species, such as sulfhemoglobin, these four analytes must total 100%.

A photoplethysmographic method according to the present invention comprises the step of generating at least approximately monochromatic beams of light having at least distinct first and second spectral contents denoted by center wavelengths $\lambda_1$ and $\lambda_2$ generated by one or more emitters. The light is then directed into a portion of the tissue of the patient in order to pass light through the tissue portion along an optical path. The method further comprises generating at least approximately monochromatic beams of light having at a minimum one additional distinct spectral content and perhaps a fourth distinct spectral content denoted by center wavelengths, $\lambda_3$ and $\lambda_4$, generated by an additional emitter or emitters, wherein each center wavelength is different from the other. This light is also directed into a portion of the tissue under test to pass through the tissue portion along substantially the same optical path. The method of the invention further comprises the use of means for detecting the received light transmitted from the tissue such as a photodiode or other appropriate detector. $I_{\lambda 1}, I_{\lambda 2}, I_{\lambda 3}$ and $I_{\lambda 4}$ are the measurements of the light received from tissue after absorption and modulation by the various absorbers in the tissue and arterial blood under test.

From the received light measurements, $I_{\lambda 1}, I_{\lambda 2}, I_{\lambda 3}$ and $I_{\lambda 4}$ the differential absorptions (generally denoted dA's) of the transmitted light by various absorbers in the blood are calculated. These differential absorptions (dA's) are then used in the estimation of the blood analyte levels by minimizing an objective function related to the error present in the estimations while satisfying certain constraints. In the case of measuring the concentration of oxyhemoglobin, reduced hemoglobin, carboxyhemoglobin and methemoglobin in the blood, the objective function is minimized while satisfying the constraints that the concentrations of the four analytes must total 100 percent and each analyte concentration must be greater than zero and less than 100 percent.

A preferred embodiment describes a method of determining the blood analyte concentrations which minimizes the computation time by inverting the initial calibration equation and using linear algebra and Lagrange multipliers.

BRIEF DESCRIPTION OF THE DRAWINGS

Preferred embodiments of the invention are described below with reference to the following drawings.

DETAILED DESCRIPTION OF THE INVENTION

Figure 1:
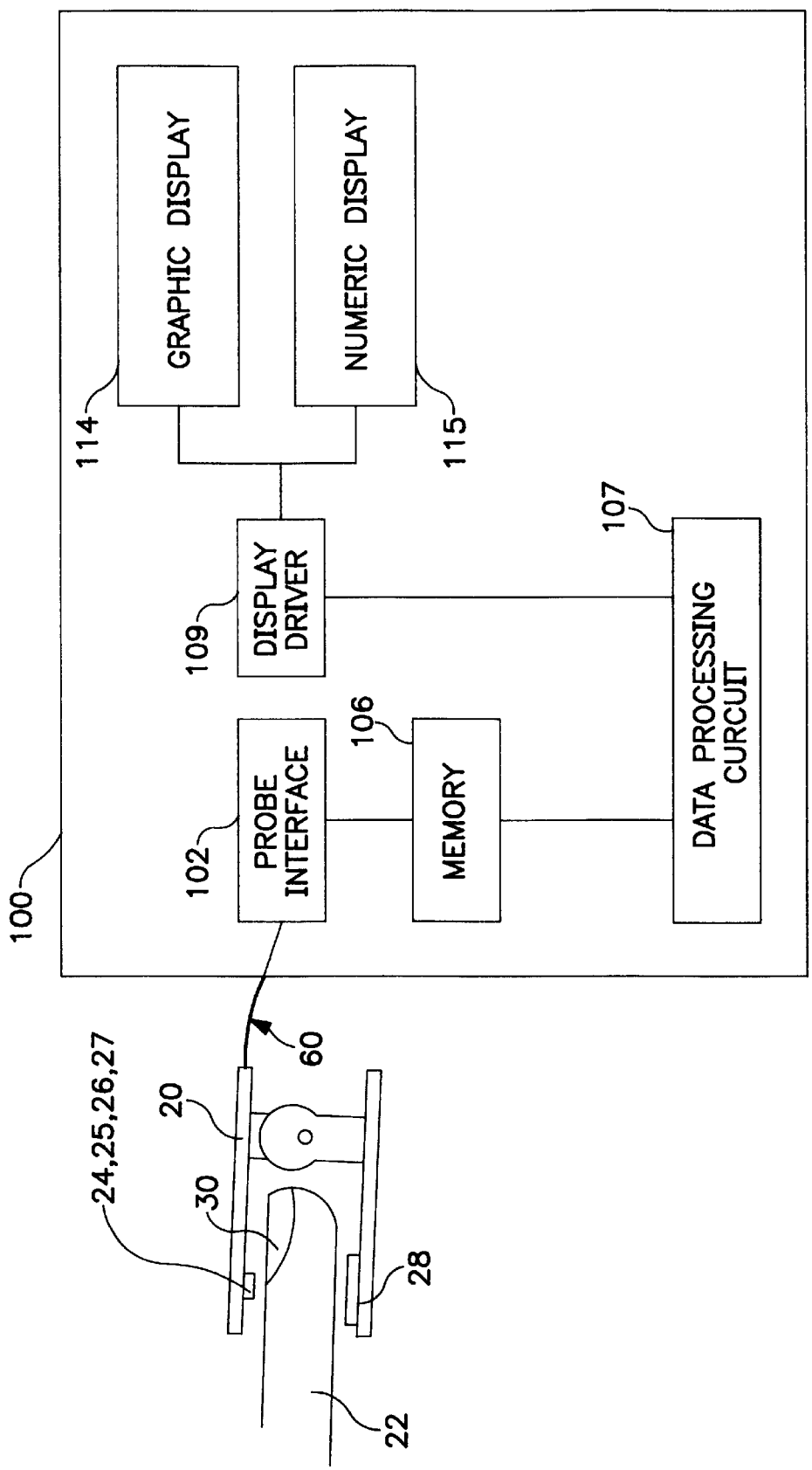
FIG. 1 is a diagram showing an embodiment of the apparatus of the claimed invention.

The photoplethysmographic monitor of the present invention measures the concentration of oxyhemoglobin (O2Hb), deoxyhemoglobin or reduced hemoglobin (RHb), carboxyhemoglobin (COHb) and methemoglobin (MetHb) in a patient's blood. This is accomplished through the use of at least two, but preferably four emitters (or a filtered broadband emitter) emitting beams of light having a spectral content characterized by center wavelengths, $\lambda_1, \lambda_2, \lambda_3$ and $\lambda_4$. The spectral content of the light emitted by the four emitters (or filtered broadband emitter) must be distinct. It is typical that the center wavelengths for the emitters are distinct so that $\lambda_1 \neq \lambda_2 \neq \lambda_3 \neq \lambda_4$. FIG. 1 depicts an apparatus made according to the present invention. Probe 20 is placed on opposite sides of tissue under test 22. Probe 20 contains a plurality of emitters 24, 25, 26, 27 (or filtered broadband light source) which each emit light having a distinct spectral content denoted by $\lambda_1, \lambda_2, \lambda_3$ and $\lambda_4$. In the case of a finger probe, the emitters are arranged to emit the light at or near the base of the fingernail 30. These emitters may be light-emitting-diodes (LED's) or laser diodes. It is also possible to filter a broadband light source to produce light having four distinct spectral contents. However, the preferred embodiment is to use at least four separate emitters each producing light with a distinct spectral content. More than four emitters may be used in order to create an overdetermined system, i.e., a system where the number of unknown blood analyte concentrations to be measured is smaller than the number of center wavelengths used. The emitters may also be housed in the monitor 100 and the emitted light may be transmitted to the probe 20 by optical fiber or other such optically transmissive material in place of the electrically conductive connector 60.

In a photoplethysmographic system of the present invention, the intensity of light transmitted through the tissue under test is measured through the use of one or more photodetectors 28 which provide a signal corresponding to the intensity of light received denoted $I_{\lambda 1}, I_{\lambda 2}, I_{\lambda 3}$ and $I_{\lambda 4}$. These intensity measurements are transmitted to a central processing unit housed in the monitor 100. In the monitor 100 the analog received intensity signals, $I_{\lambda 1}, I_{\lambda 2}, I_{\lambda 3}$ and $I_{\lambda 4}$, are converted into digital equivalents through a well-known analog to digital (A/D) converter which is part of probe interface 102. The intensity signals are then stored in memory 106 and manipulated in data processing circuit 107 of the monitor 100 according to data processing instructions stored in memory 106 and executed by the data processing circuit 107 in order to determine an estimate of the blood analyte concentrations. Blood analyte concentrations may then be displayed via display driver 109 and graphic display 114 and/or numeric display 115.

Figure 2:
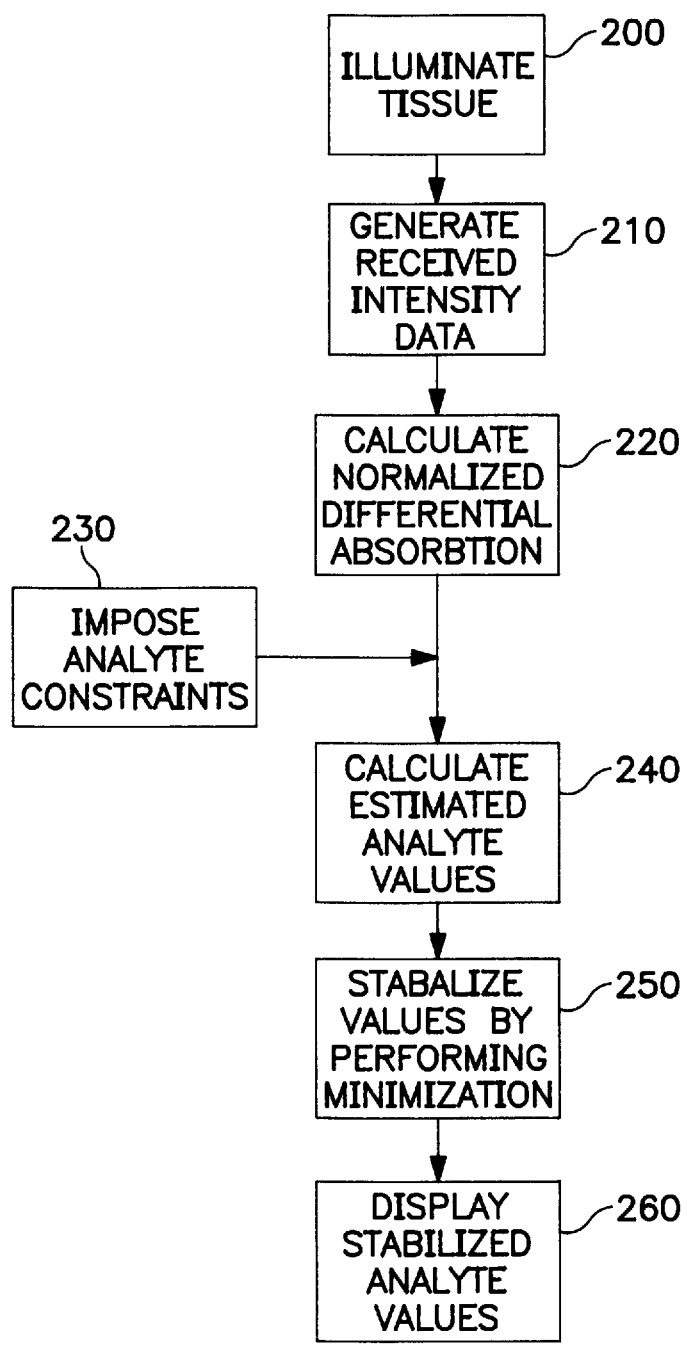
FIG. 2 is a flow diagram of the method of generating blood analyte concentrations according to the present invention.

Referring to FIG. 2 the method of generating blood analyte concentration levels according to the present invention is set forth. As described above, the first step 200 is to illuminate the tissue of the subject with the plurality of emitted light beams. Depending on the number of unknown blood analytes for which an estimate is desired, the number of emitters may vary. For a system for determining the O2Hb, RHb, COHb and MetHb levels of the tissue under test, at least four emitters are necessary. After illuminating tissue 22 (or another part of the body such as an ear lobe or nasal septum) the intensity of the light received by photodetector(s) 28 is generated. In the current embodiment of this invention, the received intensities $I_{\lambda 1}, I_{\lambda 2}, I_{\lambda 3}$ and $I_{\lambda 4}$ from each emitter are kept separate from one another by the same time division multiplexed scheme used in commercially available pulse oximeters.

For each distinct spectral content employed by the system $\lambda_1, \lambda_2, \lambda_3,$ and $\lambda_4$, the differential absorption, $dA_\lambda$ of the light for any two adjacent samples is calculated according to the following formula, for example for $\lambda_1$:

$$dA_{\lambda_1} \approx \Delta A_{\lambda_1} = \frac{[I_{\lambda_1}(t_j) - I_{\lambda_1}(t_j-1)]}{[I_{\lambda_1}(t_j) + I_{\lambda_1}(t_{j-1})]/2} \quad (1)$$

Figure 3:
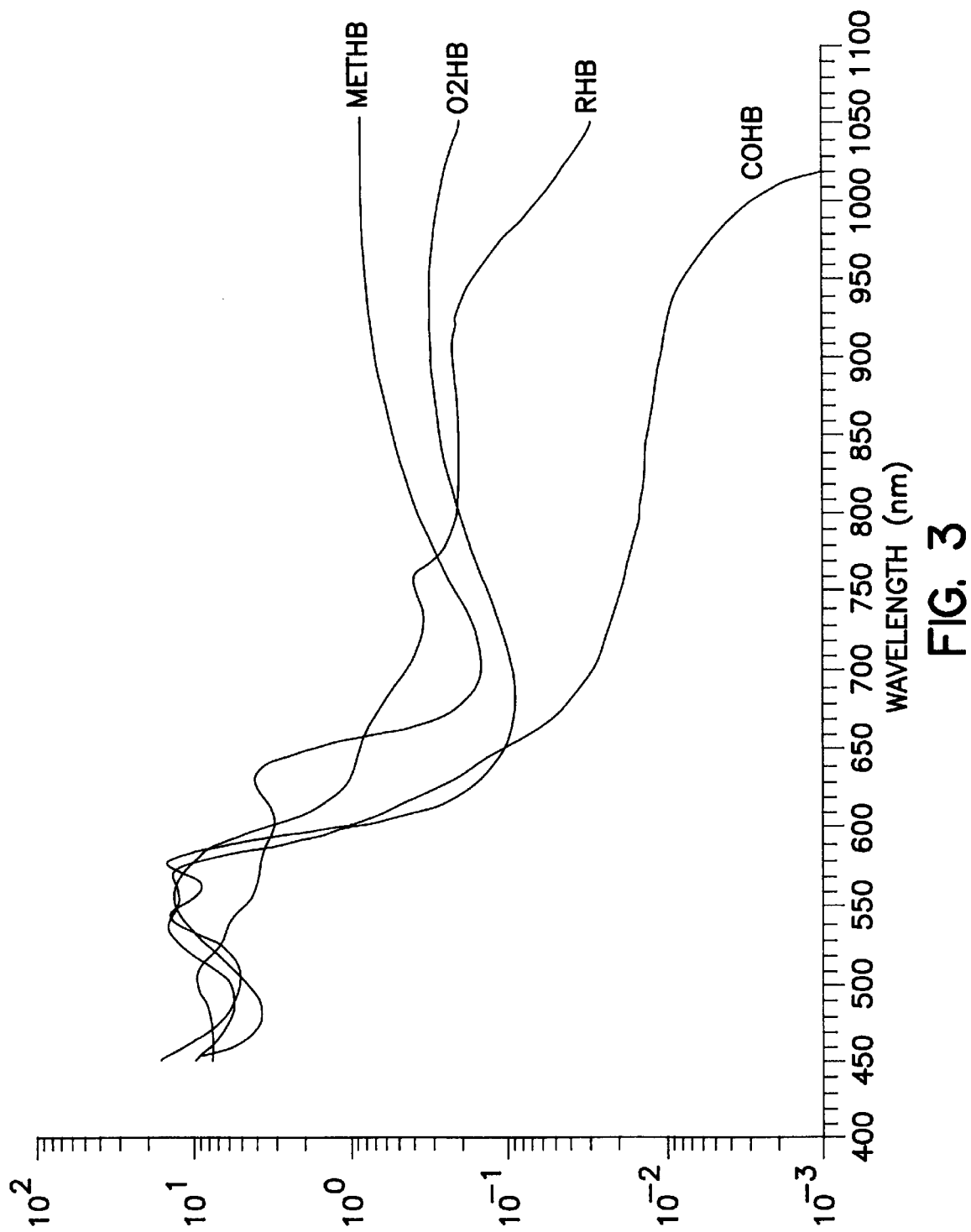
FIGS. 3 is a graph of the extinction curves of oxyhemoglobin, reduced hemoglobin, carboxyhemoglobin and methemoglobin in terms of millimolar extinction, on a logarithmic scale, versus wavelength in nanometers.

The differential absorption at wavelength X is also approximately equal to:

$$\Delta A_\lambda = E_\lambda^O C^O \Delta L^O + E_\lambda^R C^R \Delta L^R + E_\lambda^{CO} C^{CO} \Delta L^{CO} + E_\lambda^{Met} C^{Met} \Delta L^{Met} \quad (2)$$

where C is the concentration of the specific absorber, E is the extinction for that absorber at wavelength λ and ΔL is the differential effective path length the transmitted light has traveled. (Superscripts O2, R, CO, and Met refer to O2Hb, RHb, COHb, and MetHb respectively.) Thus, after measuring the received light intensities, knowing the extinction coefficient E for each wavelength, and assuming a compartmentalized model where the concentration C of all analytes is the same constant value, it is possible to determine the relative percent concentration of a specific absorber xHb as the incremental change in path length for that absorber $\Delta L^x$ divided by the total change in path length $\Delta L^O + \Delta L^R + \Delta L^{CO} + \Delta L^{Met}$. FIG. 3 shows the extinction curves of oxyhemoglobin, reduced hemoglobin, carboxyhemoglobin and methemoglobin in terms of millimolar extinction, on a logarithmic scale, versus wavelength in nanometers.

A number of alternate methods may be used for computing the differential absorption (1) and such methods are included within the scope of this invention. As one skilled in the art will understand, $t_{j-1}$ and $t_j$ need not be consecutive samples in time. In one such alternate method, $t_{j-1}$ may correspond to a valley on transmitted intensity waveform while $t_j$ corresponds to a peak on the transmitted intensity waveform so that peak to peak changes in transmitted intensity are used to compute $\Delta I_\lambda(t)$. In addition, instead of averaging $I_\lambda(t_{j-1})$ and $I_\lambda(t_j)$ in the denominator of (1), a long term average over many data points may be used.

In the present invention, normalized differential absorptions are used to obtain the analyte concentration values. From the differential absorptions, $dA_{\lambda 1}$, $dA_{\lambda 2}$, $dA_{\lambda 3}$ and $dA_{\lambda 4}$, normalized differential absorptions are computed by taking the ratio of differential absorptions from two different emitters. For example, for center wavelengths $\lambda_2$ and $\lambda_1$, the normalized differential absorption is computed as $$N_{21} = dA_{\lambda 2}/dA_{\lambda 1}. \quad (3)$$

These normalized differential absorptions (normalized dA's) may be computed in a number of different ways. In particular, instead of simply taking a ratio, the normalized dA (3) may also be computed as the slope of the regression line obtained from least squares regression by regressing $dA_{\lambda 2}$ on $dA_{\lambda 1}$. As one skilled in the art will understand suck alternative methods for computing the normalized differential absorptions such as that described in U.S. Pat. No. 5,503,148 are hereby incorporated by reference.

The normalized dA's are then used in a calibration equation to obtain the measured analyte values. In one embodiment of the present invention, the calibration equation is given by $$xHb = \frac{a_1 + a_2 N_{21} + a_3 N_{31} + a_4 N_{41}}{b_1 + b_2 N_{21} + b_3 N_{31} + b_4 N_{41}} \quad (4)$$

where xHb refers to one of O2Hb, RHb, COHb, or MetHb, the constants, $a_1$, $a_2$, $a_3$, $a_4$, $b_1$, $b_2$, $b_3$, and $b_4$ are calibration coefficients determined previously in a calibration experiment, and $N_{21}$, $N_{31}$, and $N_{41}$ are normalized dA's for channels 2 and 1, 3 and 1, and 4 and 1, respectively. As one skilled in the art will understand, however, the calibration equation for each analyte is not limited to this form of equation, and may be, for example, a polynomial.

Figure 4:
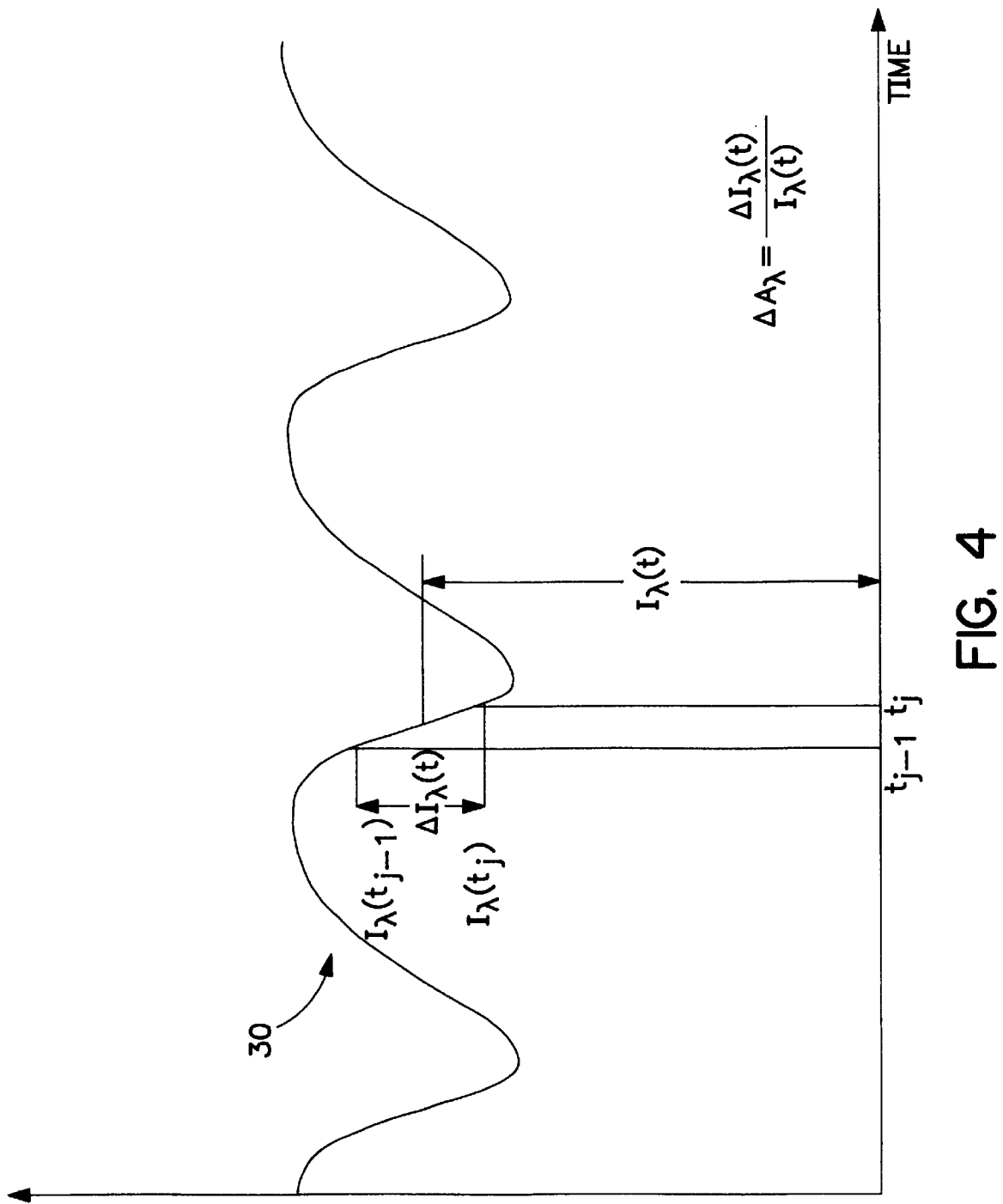
FIG. 4 is a graph showing the sampled received intensity signals from the sensor of FIG. 1.

A graph of the received intensity signal, $I_\lambda$, 30 versus time can be seen in FIG. 4 As can be seen from the above equations, errors occurring in the measurement of the received light intensities, $I_{\lambda 1}$, $I_{\lambda 2}$, $I_{\lambda 3}$ and $I_{\lambda 4}$ will directly affect the normalized dA and, therefore, the calculation of the estimated blood analyte concentration. For unknown analyte concentrations, the next step in FIG. 2 is to calculate the normalized dA's 220 from the received light intensity data and to then calculate the estimated analyte values for O2Hb, RHb, COHb and MetHb 240.

Prior art techniques for estimating the analytes O2Hb, RHb, COHb, and MetHb would simply involve obtaining the estimates according to, for example, equation (4) and displaying the result. However, the analyte estimates may be less than 0% or greater than 100%, and may not total 100%. If this is the case, then some error source is significantly affecting measurement accuracy. In an attempt to minimize the effects such error sources, the present invention requires more than the prior art techniques in that a set of analyte constraints is imposed 230. In the four analyte system, the preferred constraints require that the analyte concentrations total 100 and that no analyte concentration is less than zero or greater than 100. Other possible constraints would be the use of ranges for a specific analyte concentration value. For example the value for MetHb could be constrained to be greater than or equal to zero but no greater than 35 percent.

In a system designed to find four blood analyte concentrations the method and apparatus of the present invention subjects the first estimated values for oxyhemoglobin, reduced hemoglobin, carboxyhemoglobin and methemoglobin to the following minimization procedure, step 250, where analytes denoted by subscript 1 are the original estimates computed from, for example, equation (4), and analytes denoted by subscript 2 are the final stabilized analyte estimates which conform to the specified constraints and minimize the objective function:

$$\text{minimize } [c_1(O2Hb_2 - O2Hb_1)^2 + c_2(RHb_2 - RHb_1)^2 + c_3(COHb_2 - COHb_1)^2 + c_4(MetHb_2 - MetHb_1)^2] \quad (5)$$

subject to two constraints:
 (a) $O2Hb_2 + RHb_2 + COHb_2 + MetHb_2 = 100$, and
 (b) each of the analyte concentrations $O2Hb_2$, $RHb_2$, $COHb_2$, $MetHb_2$ must be greater than or equal to zero.

The additional condition that each of the analyte concentrations is less than or equal to 100 is unnecessary because if all of the analyte measurements are greater than zero and sum to 100 percent then they each must also be less than 100 percent.

Constants $c_1$, $c_2$, $c_3$ and $c_4$ are weights assigned to each blood analyte reflecting the relative accuracy and stability of the initial measurement for that analyte. For example, the initial accuracy in measuring MetHb and RHb is generally quite high so the constants $c_2$ and $c_4$ are correspondingly large. On the other hand, the initial accuracy of COHb is generally quite low so the constant $c_3$ is set to be correspondingly low. By assigning constants in this manner, the analytes with the lowest accuracy are allowed to deviate further from their initial value than the analytes with the highest initial accuracy throughout the minimization procedure. This methodology for choosing constants $c_1$, $c_2$, $c_3$ and $c_4$ generally gives the highest degree of overall accuracy in measuring O2Hb, RHb, COHb, and MetHb.

By using well-known optimization techniques, the objective function is minimized subject to the constraints in order to determine the set of analyte concentration values which most accurately reflects the actual concentrations. Examples of such techniques include the following iterative linear or nonlinear programming techniques: simplex, Karmarkar, steepest descent, gradient projection, penalty function, barrier function, simulated annealing, and genetic algorithms. These stabilized analyte values can then be displayed 260 to the user as a more accurate estimation of the actual blood analyte concentrations.

Table 1 sets forth the improvement seen in the estimated analyte levels using the above described stabilization method and apparatus.

TABLE 1

| constants $c_1, c_2, c_3, c_4$ | Result | O2Hb Estimate | RHb Estimate | COHb Estimate | MetHb Estimate |
|---|---|---|---|---|---|
| calibration only | MAE | 7.20 | 2.70 | 6.06 | 1.37 |
| | BIAS | 1.65 | 0.464 | −0.362 | 0.169 |
| | SDPD | 9.22 | 3.55 | 8.03 | 1.80 |
| 15, 45, 1, 45 analyte stabilization | MAE | 6.06 | 2.65 | 4.84 | 1.23 |
| | BIAS | 0.631 | 0.100 | −0.571 | 0.158 |
| | SDPD | 7.73 | 3.72 | 6.06 | 1.76 |

Figure 5:
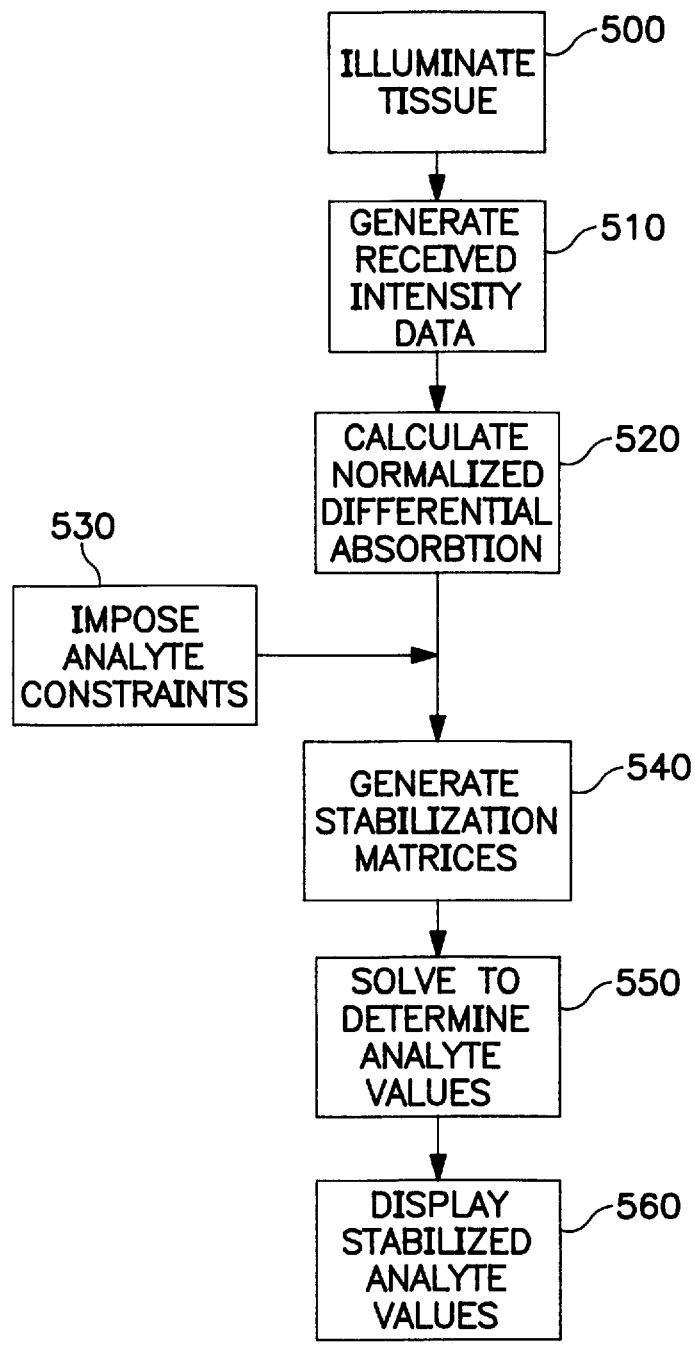
FIG. 5 is a flow diagram of a preferred alternate method of generating blood analyte concentrations according to the present invention.

An alternate method of stabilizing blood analyte concentration values employs an alternate form of calibration equation along with the techniques of linear algebra to simplify the stabilization process. FIG. 5 depicts this alternate embodiment of the method and apparatus. The steps of illuminating the tissue 500, generating received intensity data 510, calculating normalized differential absorptions 520 and imposing predetermined analyte constraints 530 remain essentially identical to aforedescribed method. In this embodiment, the iterative minimization process is replaced by the generation 540 and solution 550 of a set of stabilization matrices corresponding to minimization of an error function generated from inverse calibration equations as defined below. The resulting stabilized analyte concentration values may be displayed 560 after generation.

The aforementioned alternate method of calculating corrected blood analyte concentrations uses an inverted form of the calibration equation relating the analytes to be measured to the normalized dA presented in equation (3):

$$N_{ij} = \frac{(a_1 O2Hb + a_2 RHb + a_3 COHb + a_4 MetHb)}{(b_1 O2Hb + b_2 RHb + b_3 COHb + b_4 MetHb)} \quad (6)$$

$N_{ij}$ is the normalized dA for channel i over channel j and $a_1$ through $a_4$ and $b_1$ through $b_4$ are constants determined from the extinction properties of the four hemoglobin at channels i and j. The inverted form of equation (6) is easier to manipulate than the form of equation (4). Additionally, calibration equations of this form more closely follow the statistical assumption of least squares regression which assumes that the experimental error is present in the y variable (N) and not in the x variables (O2Hb, RHb, COHb, MetHb). In order to calculate the analyte concentrations for four analytes, xHb where x=O2, R, CO and Met, six equations of the form (6) are used—one for each of the six different wavelength combinations. For each equation, constants $a_1$ through $a_4$ and $b_1$ through $b_4$ are constants determined through nonlinear regression in a previous calibration experiment, i.e., by measuring $N_{ij}$; i,j=1,2,3,4 for known analyte levels and selecting these coefficients to minimize some error.

It is an aspect of the present invention that the calibration coefficients in (4) and (6) are not unique. In particular, as one skilled in the art will understand.. by multiplying all of the constants $a_1$ through $a_4$ and $b_1$ through $b_4$ by some constant value, the error in the resulting calibration equation will remain unchanged.

In this embodiment of the present invention, the minimization problem is formulated as follows. Find O2Hb, RHb, COHb, and MetHb which $$\text{minimize } E_{ij}(N_{ij:2} - N_{ij:1})^2 \quad (7)$$

subject to two constraints:
 (a) O2Hb+RHb+COHb+MetHb=100, and
 (b) each of the analyte concentrations O2Hb, RHb, COHb, MetHb must be greater than or equal to zero.
where $N_{ij:1}$ is the measured normalized dA for channels i and j, and $N_{ij:2}$ is the normalized dA estimated by using equation (6) and the analyte estimates O2Hb, RHb, COHb, and MetHb.

By using matrix notation, this minimization problem can be solved without using an iterative process. Therefore, the following notation is introduced. Let N be a 6×1 column vector containing the six normalized differential absorption values. Matrices A and B are 4×6 matrices whose ith column contains the four calibration coefficients for the ith row of N. Matrix xhb=[O2Hb RHb COHb MetHb]T, i.e., the four analyte estimates. Using this notation, the minimization problem can be formulated as follows:

$$\text{minimize } [N-[\text{diag}(B^T xHb)]^{-1} A^T xHb]^T [N-[\text{diag}(B^T xHb)]^{-1} A^T xHb] \quad (8)$$

subject to two constraints:
 (a) $xHb^T e = 100$, and
 (b) $xHb \geq 0$.

where diag(x) is a matrix whose diagonal elements contain the elements of the vector x and whose off diagonal elements are zero, superscript −1 denotes the standard matrix inverse, and e denotes a 4×1 column vector of all ones.

As with the previous embodiment of the present invention, it is also within the scope of the present invention that the objective function may contain weights which reflect the initial accuracy of the calibration equations (6) used in this embodiment. In matrix notation, this corresponds to having an additional 6×6 matrix V so that the objective function becomes the following:

$$\text{minimize } [N-[\text{diag}(B^T xHb)]^{-1} A^T xHb]^T V [N-[\text{diag}(B^T xHb)]^{-1} A^T xHb]. \quad (9)$$

The best analyte estimations are then calculated in a straightforward manner using Calculus and Lagrange multipliers. The objective function is multiplied by diag($B^T$ xHb) transforming the objective function into a quadratic function so that the resulting system of equations to be solved is simple, linear and optimal.

By using Lagrange multipliers and Calculus, an explicit solution to this minimization procedure can be obtained. In particular, the analytes can be determined from the following equation where K=diag (N) $B^T - A^T$ and e is a 4×1 column vector of ones.

$$\underline{xHb} = \frac{100}{\underline{e}^T (\underline{K}^T \underline{K})^{-1} \underline{e}} (\underline{K}^T \underline{K})^{-1} \underline{e} \quad (10)$$

This preferred embodiment of the present method and apparatus has significant advantages over the previous embodiment. In particular, the analyte estimates are obtained explicitly without the need for an iterative algorithm. This saves computation time and makes the approach more amenable to implementation in a continuous, real-time instrument.

Table 2 set forth below provides the result of a study to determine the impact the use of the method had on analyte concentration estimates. The mean absolute error (MAE), standard deviation of error (SDPD) and bias (BIAS) of the resulting analyte estimates have been provided. Actual blood analyte data was taken using the OSM3 Hemoximeter.

TABLE 2

| Data Set | Error Measure | O2Hb | RHb | COHb | MetHb |
|---|---|---|---|---|---|
| calibration only | MAE | 4.72 | 1.56 | 6.15 | 0.86 |
| | SDPD | 7.17 | 2.33 | 7.61 | 1.25 |
| | Max error | 23.1 | 5.41 | 26.8 | 4.30 |
| analyte stabilization | MAE | 3.63 | 1.07 | 3.88 | 0.71 |
| | SDPD | 5.17 | 1.07 | 5.85 | 1.19 |
| | Max error | 16.91 | 3.49 | 20.30 | 4.17 |

It is within the scope of the present invention that the two methods disclosed here may be generalized to the case where one or more analyte concentration is substantially known a priori. For example, if the MetHb concentration has already been estimated before implementation of this method and is assumed to be highly accurate, then it can be placed into the minimization procedure (5) or (8) as a constant value. As a result, only the O2Hb, RHb, and COHb concentrations will be estimated. In the case of the preferred embodiment presented here, the closed form solution to the minimization procedure (10) will be modified slightly. For the example presented here, the solution becomes $$\tilde{x} = \frac{100 - MetHb + MetHb[\underline{e}^T(\underline{K}_3^T\underline{K}_3)^{-1}\underline{K}_3^T\underline{c}_4]}{\underline{e}^T(\underline{K}_3^T\underline{K}_3)^{-1}\underline{e}} (\underline{K}_3^T\underline{K}_3)^{-1}\underline{e} - MetHb(\underline{K}_3^T\underline{K}_3)^{-1}\underline{c}_4 \quad (11)$$

where $\tilde{x}=[O2Hb\ RHb\ COHb]^T$, MetHb is the a priori estimate of methemoglobin concentration, $K_3$ is a 6×3 matrix containing the first three columns of K, and $c_4$ is a 6×1 column vector containing the fourth column of K.

While the example of a preferred embodiment above is provided for a non-invasive photoplethysmographic monitor which measures the concentration of oxyhemoglobin, reduced hemoglobin, carboxyhemoglobin and methemoglobin in the blood., the present system can be used to improve the stability in measuring any system with noise present in the measurement data, where the concentrations of analyte or other parameters have a known physical relationship to one another. For example some possible relationships include, for analytes $y_1, y_2, y_3, y_4 \ldots y_n$:

$$a_1y_1+a_2y_2+a_3y_3+a_4y_4+ \ldots a_ny_n=k \quad (12)$$

$$y_j \geq k, \text{ for any } j=1, 2, \ldots n \quad (13)$$

$$y_iy_j=k \text{ for any } i, j=1, 2, \ldots n \quad (14)$$

The proposed methodology generalizes to the following: Find $x_1, x_2 \ldots x_n$ by solving $$\min (y_1-x_1)^2+(y_2-x_2)^2+ \ldots +(y_n-x_n)^2 \quad (15)$$

$$\text{subject to } f(x_1, x_2, x_3, \ldots x_n) \in S \quad (16)$$

where $y_1, y_2, y_3, y_4 \ldots y_n$ are the initial estimates or measurements and $x_1, x_2 \ldots x_n$ are the modified estimates and $f(x_1, x_2, x_3, \ldots x_n) \in S$ specifies the relationship between the analytes to be used as constraints in the minimization procedure.

While various embodiments of the present invention have been described in detail, it is apparent that modifications and adaptations of those embodiments will occur to those skilled in the art. For example, it should be appreciated that the method and apparatus as taught by the present invention may be modified in an unlimited number of ways within the framework of the teachings of the present invention. These variations are all considered to fall within the scope of the present invention provided only that the false charge reduction concepts as taught herein are applied. Therefore, it is to be expressly understood that such modifications and adaptations are within the spirit and scope of the present invention, as set forth in the following claims

I claim:

1. A method for measuring a concentration value for each of a plurality of blood analytes in a portion of tissue of a patient comprising the steps of:
   a. generating a plurality of light beams each having a distinct spectral content;
   b. directing each of the plurality of light beams into the portion of tissue;
   c. detecting light transmitted through the portion of tissue to generate a plurality of received light intensity signals representative of the detected light for each of the plurality of light beams;
   d. calculating an estimated blood analyte concentration value from the plurality of received light intensity signals for each of the plurality of blood analytes by minimizing an error function associated with said estimated blood analyte concentration values while satisfying a predetermined set of constraints placed on said estimated blood analyte concentration values.

2. The method according to claim 1 wherein a first constraint in the set of constraints is that each of the estimated blood analyte concentration values must fall within a predetermined range.

3. The method according to claim 2 wherein the predetermined range requires each estimated blood analyte concentration value to exceed 0 and to be below 100.

4. The method according to claim 2 wherein a second constraint in the set of constraints is that the sum of all of the estimated blood analyte concentration values must equal 100.

5. The method according to claim 1 wherein the step of calculating the estimated blood analyte concentration values further comprises:
   (i) generating a set of closed form equations in a stabilization matrix;
   (ii) solving the set of closed form equations in the stabilization matrix.

6. The method according to claim 1 wherein the step of calculating the estimated blood analyte concentrations further comprises:
   (i) generating normalized differential absorption values from the plurality of received light intensities;
   (ii) calculating an estimate for each blood analyte concentration value from the normalized differential absorption values;
   (iii) determining if error in the estimated blood analyte concentration values is minimized; and,
   (iv) repeating steps (ii) and (iii) until the error is minimized.

7. An apparatus for the generation of stabilized blood analyte concentration values corresponding to the concentration of a plurality of blood analytes in a tissue portion of a patient comprising:
   one or more emitters which illuminate the tissue portion of the patient with a plurality of light signals each having a distinct spectral content;

a photodetector which detects the light transmitted through the tissue portion and generates a plurality of received light intensity signals;

a microprocessor;

a means for communicating said plurality of received light intensity signals from the photodetector to said microprocessor;

wherein said microprocessor executes a series of computer program instructions thereby calculating an estimated analyte value from the plurality of received light intensity signals while minimizing error associated with said estimated analyte values and while satisfying a set of constraints placed on said estimated analyte values.

8. The apparatus for generation of stabilized blood analyte concentration values according to claim 7 wherein one emitter emits a plurality of light signals each having distinct spectral contents.

9. The apparatus for generation of stabilized blood analyte concentration values according to claim 7 wherein said one or more emitters comprise a plurality of emitters and said plurality of emitters each emit one light signal of the plurality of light signals each having a distinct spectral content.

10. The apparatus for generation of stabilized blood analyte concentration values according to claim 7 further comprising a display wherein the stabilized analyte concentration values are displayed to a user.

11. The apparatus for generation of stabilized blood analyte concentration values according to claim 7 further comprising a user input device whereby a user inputs the set of constraints.

12. The apparatus for generation of stabilized blood analyte concentration values according to claim 7 wherein said microprocessor executes a series of computer program instructions for generating a stabilization matrix comprising a set of closed form equations and for calculating the stabilized blood analyte concentration values from said stabilization matrix.

13. The apparatus for generation of stabilized blood analyte concentration values according to claim 7 wherein said microprocessor calculates the stabilized blood analyte concentration values by iteratively calculating an estimated analyte concentration value until the error function is minimized while satisfying the set of constraints.

* * * * *